United States Patent [19]

De Jong

[11] 4,384,935
[45] May 24, 1983

[54] GAS ANALYSIS APPARATUS

[75] Inventor: Herman L. De Jong, Eindhoven, Netherlands

[73] Assignee: U.S. Philips Corporation, New York, N.Y.

[21] Appl. No.: 181,287

[22] Filed: Aug. 25, 1980

[30] Foreign Application Priority Data

Sep. 13, 1979 [NL] Netherlands .................. 7906833

[51] Int. Cl.³ ........................................... G01N 27/58
[52] U.S. Cl. .................. 204/406; 204/425; 204/426
[58] Field of Search ........................ 204/195 S, 1 S

[56] References Cited

U.S. PATENT DOCUMENTS

| 3,514,377 | 5/1970 | Spacil et al. | 204/195 S X |
| 3,650,934 | 3/1972 | Hickham et al. | 204/195 S |
| 3,698,384 | 10/1972 | Jones | 204/195 S X |
| 3,699,032 | 10/1972 | Rapp | 204/195 S |
| 3,907,657 | 9/1975 | Heijne et al. | 204/195 S |
| 3,923,624 | 12/1975 | Beekmans et al. | 204/195 S |
| 4,088,543 | 5/1978 | Ruka | 204/1 T |
| 4,158,166 | 6/1979 | Isenberg | 204/195 S X |
| 4,272,329 | 6/1981 | Hetrick et al. | 204/1 T |
| 4,272,330 | 6/1981 | Hetrick | 204/1 T |
| 4,272,331 | 6/1981 | Hetrick | 204/1 T |

Primary Examiner—G. L. Kaplan
Attorney, Agent, or Firm—Robert T. Mayer; Bernard Franzblau

[57] ABSTRACT

A gas analysis apparatus employing partitions with ionic conduction which, instead of using a capillary opening or a semi-permeable membrane to fill a measuring space by means of a continuous diffusion process, employs the partition (8, 8a) which is used for rapidly emptying a measurement space (7, 7a) also for filling the measurement space up to the concentration to be measured. For this purpose a pumping current ($i_p$) is replaced by a filling current ($i_v$) of opposite polarity.

22 Claims, 4 Drawing Figures

GAS ANALYSIS APPARATUS

The invention relates to a gas analysis apparatus for measuring the concentration of a gaseous component in a first space. This type of apparatus may include a measurement space having at least one wall portion comprising a partition which at least partly separates the measurement space from the first space and which comprises at least one solid substance exhibiting ionic conduction and both sides of which are provided with at least one electrode layer. These layers are connected to a control unit which periodically applies a pumping current to the partition during a pumping time interval $t_p$. So that by means of a current of ions in the partition, the gaseous component is removed from the measurement space. Subsequently the measurement space is refilled to the concentration to be measured in a filling time interval $t_v$ and the electric charge transferred in the partition is measured to derive an indication of the concentration of the gaseous component. A detection circuit is connected to electrode layers of the partition to produce an interrupt signal for interrupting the current supplied by the control unit in the case of a specific voltage variation between said electrode layers.

Such a gas analysis apparatus is known from U.S. Pat. No. 3,907,657. In addition to the various constructions for the measurement space and the methods of electrically measuring a charge, the U.S. Patent also describes the use of one or two partitions which operate either with or without a reference atmosphere. In embodiments with one partition, said partition may be provided with a plurality of electrode layers on both sides in order to perform various electrically isolated measurements, such as measurement of the temperature, or resistance of the partition and the Nernst voltage across the electrode layers. In all embodiments there is provided a partition which receives a pumping current and by means of which the relevant gaseous component can be removed from the measurement space through the ion migration in the partition. The electrode layers, to which the pumping current is applied, may be used for signalling that the measurement space is substantially empty. Separate electrode layers may be arranged on the partition to provide this signalling function, or a separate, i.e. an additional, partition may be provided for this purpose. In the known apparatus the measurement space is rapidly emptied and subsequently it is slowly refilled by diffusion up to the concentration to be measured. This means that the filling time interval $t_v$ is several times, for example a factor of 10, as great as the pumping time interval $t_p$, which yields the actual measuring data.

It is an object of the invention to equalize these time intervals or even to make the filling time interval smaller than the pumping time interval.

The invention is based on the recognition that the partition, by means of which the measurement space is emptied, can also be used for filling said space. Furthermore, the measurement space may then be hermetically sealed and will have no capillary openings or semipermeable membranes through which a continuous diffusion occurs.

To this end a gas analysis apparatus of the aforementioned type is characterized in that the control unit supplies a filling current to the partition in the filling time interval, which current is of a polarity opposite to that of the pumping current. The detection circuit comprises a first voltage detector which is connected to electrode layers of the partition and supplies a filling-interrupt signal for interrupting the filling current when the voltage across said electrode layers has reached a first reference value at which the concentration of the gaseous component on both sides of the partition is substantially the same.

In this respect it is therefore an advantage of the invention that the capillary openings or semipermeable membranes are avoided and a very rapidly responding measuring apparatus is obtained. In practice it is possible to achieve, for example, a gain of time by a factor of 1000, which mainly resides in the fact that the measurement space can now be made very small, for example with a capacity of half a cubic millimeter. In the known apparatus this is not possible because a corresponding capillary opening would be impractically small.

In a particular embodiment of the invention the same electrode layers are used in order to detect whether the measurement space is empty or filled, employing two voltage detectors with associated reference values. A flip-flop may be used so that an astable circuit arrangement is obtained and, for example, the period of the pulse train thus obtained is a measure of the concentration to be measured. A more accurate detection can also be obtained if the Nernst voltage is measured with the aid of an additional partition, the filling and pumping currents being applied to the other partition.

The invention will be described in more detail with reference to the drawing. In the drawing:

FIG. 1 shows two embodiments and an electrical block diagram of an apparatus in accordance with the invention, FIG. 2 shows a more detailed circuit diagram of an arrangement with a flip-flop, FIG. 3 represents a diagram associated with FIG. 2, and FIG. 4 represents a time diagram which is also associated with FIG. 2.

FIG. 1 shows a first space in the form of a tube 1 through which gases are passed, for example exhaust gases of an internal combustion engine. A gaseous component is measured by means of a transducer 2 which is arranged in the wall of the tube 1 by fixing means 3. A first partition 4 is in contact with the gases with the side on which the porous electrode layer 5 is arranged. The other side with the electrode layer 6 forms a part of the wall of a measurement space 7. A second partition 8 constitutes another part of the wall of the measurement space. The electrode layer 9 is in contact with the electrode layer 6 by means of a ring 10, which is also in contact with the fixing means 3, which in turn has an electrical connection 11 with the terminal 12. On the outside the wall 8 is covered with an electrode layer 13 having an electrical connection 14 and a terminal 15. The two walls (partitions) are made of the same material, for example zirconium oxide. The electrode layers 5, 6, 9 and 13 and the ring 10 are made of platinum and the gaseous component which is then measured is oxygen. The ambient air around the tube 1 may be used as a reference atmosphere. The electrode layer 5 is connected to a terminal 18 with a connection 16 and a lead-through 17.

FIG. 1 also shows a transducer which is not incorporated in the wall of a first space or of a tube, but which is completely surrounded by the gases. Parts of this transducer which correspond to those of the transducer 2 are designated by the same reference numerals with the affixed letter a. The tube 1a now contains the transducer 2a comprising a measurement space 7a of which a wall portion is the partition 8a, which is provided with electrode layers 9a and 13a which are respectively connected to terminals 12a and 15a. There may be provided an electrode layer 5a, which is connected to terminal 18a. A voltage between terminal 18a and terminal 15a is a measure of the concentration or pressure ratio between the gaseous component in the measurement space and the gaseous component in the first space constituted by the interior of the tube 1a. The electrode layer 5a may be combined with the layer 9a so that terminal 18a may be dispensed with. The measurement voltage is then available between terminal 12a and 15a, and as the case may be, diminished by a voltage which represents the voltage drop caused by the filling current and the pumping current across the internal resistance of the partition. If for example, the currents are applied in the form of pulses, it is also possible to determine the voltage in the currentless periods. As the terminals 12a, 15a and 18a correspond to terminals 12, 15 and 18, the following description of the electrical block diagram applies to both transducers 2 and 2a.

A current supply unit 19 is connected to a common line 21 by a connection 20, which line is also connected to the terminal 12 and to a detection circuit 22. Via a change-over device 23 the terminal 15 is connected to the current terminal 24 or to the current terminal 25. In the shown position of the change-over device 23 a pumping current, represented by the arrow $i_p$, flows from the current supply unit 19 through the partition 8, namely from electrode layer 13 to electrode layer 9. For zirconium oxide this means that a current of negative oxygen ions is obtained from the layer 9 to the layer 13. This is possible because oxygen molecules from the measurement space 7 diffuse in the partition and oxygen molecules are delivered to the surrounding atmosphere at the location of the layer 13. The reverse will take place, i.e. the measurement space will be filled with oxygen, when the current direction is reversed. The change-over device 23 will then be in the position shown dashed and the filling current $i_v$ flows in accordance with the arrow. The change-over device is actuated by the detection circuit 22, which has an input 26 connected to terminal 18, so that the Nernst voltage of the partition 4 can be measured. By comparison with two references the instants can be determined at which the filling or the pumping current is to be interrupted and the other current is to be applied again, as the case may be immediately or after a specific time. This is symbolically represented by point 27 in the change-over device.

FIG. 2 shows an embodiment of the current supply unit 19 and the detection circuit 22.

The filling and the pumping current are supplied by two adjustable current mirrors 28 and 29. The current mirror 28, which supplies the pumping current $i_p$, comprises two pnp transistors 30 and 31, of which 31 functions as a reference diode and can be turned on and turned off by a voltage at a terminal 33 via a resistor 32. The current mirror 29 comprises two npn transistors 34 and 35, of which 35 is the reference diode which can be turned on and turned off via a resistor 36 which is also connected to terminal 33. The two current mirrors are included in series between two power supply lines 37 and 38. By making the potential of terminal 33 substantially equal to the potential of line 37, the current mirror 28 and thus the pumping current is blocked and the current mirror 29 supplies the filling current. By making the potential of terminal 33 substantially equal to the potential of line 38, current mirror 29 is blocked and the pumping current is supplied by the current mirror 28. In order to obtain a well-defined potential relative to the current mirrors for the interconnected electrode layers 6 and 9, which are connected to the terminal 12, a voltage divider is included between the supply lines 37 and 38. The divider comprises the resistors 39 and 40 in the one branch and the resistor 41 in the other branch. The junction point 42 is connected to the one input 43 of an operational amplifier 44, whose other input 45 is connected to the terminal 12, which is also connected to the junction point 46 of the emitters of two series-connected transistors 47 and 48. The bases of these transistors are connected to the output of amplifier 44, while the collector of one is connected to the line 37 and the collector of the other to the line 38. This stabilised power supply circuit ensures that at terminal 12 an incoming or outgoing current can be obtained, while the potential of terminal 12 remains equal to that of point 42.

The detection circuit 22 comprises a first voltage detector 49 in the form of an operational amplifier which is connected to the junction point 42 with its non-inverting input and which is connected to terminal 18 with its inverting input. At output 50 a filling-interrupt signal is available which is positive and can be compared with the potential of line 37 as soon as the potential at the inverting input, i.e. the potential of terminal 18, is equal to the potential at point 42, i.e. the potential of terminal 12. The electrode layers 5 and 6 then have the same potential and the filling process may be stopped. A second voltage detector 51 also takes the form of an operational amplifier having a non-inverting input connected to terminal 18 and an inverting input connected to the junction point 52 of the resistors 39 and 40, and having an output 53 which supplies a positive signal as a pumping-interrupt signal when the potential of terminal 18 becomes positive relative to the potential of junction point 52. The two voltage detectors supply a negative signal which substantially corresponds to the potential of line 38 when the interrupt signals are zero, i.e. are absent. The outputs of the detectors are connected to the control inputs of a flip-flop 54, whose Q-output is connected to the terminal 33. The supply lines of the flip-flop are connected to lines 37 and 38 so that the signals from and to the flip-flop are related to the potentials on lines 37 and 38, which in this context will be referred to as "1" and "0" respectively.

Flip-flop 54 has a set input S, which is connected to output 53 and which is 1 if the pumping-interrupt signal is present, so that Q=1, and also a reset input R, which is connected to output 50 and which is 1 if the filling-interrupt signal appears, so that Q=0. The operation of the flip-flop and the detection circuit and the relationship with the voltage Vbc across the partition 4 is illustrated in the diagram of FIG. 3, the electrode layer 5 being designated b, the layers 6 and 9 being designated c and the layer 13 being designated a, as indicated in FIG. 2.

In FIG. 3 the voltage Vbc is plotted along the vertical axis and the time along the horizontal axis. It is possible to distinguish three ranges which are separated from each other by a first reference value RW 1, which substantially corresponds to a volage O, and the second reference value RW 2. It is indicated which signals occur in each range for the S and R inputs and the Q output of the flip-flop. Since Q determines which current will flow, this is also indicated and thus the variation of Vbc as a function of time.

FIG. 4a represents two pressures $p_1$ and $p_2$, which may for example apply to oxygen in air: $p_1 = 150$ mm mercury pressure and $p_2 = 75$ mm mercury pressure, or each a factor of 10 smaller for oxygen in exhaust gases of an internal combustion engine.

Figure 1:
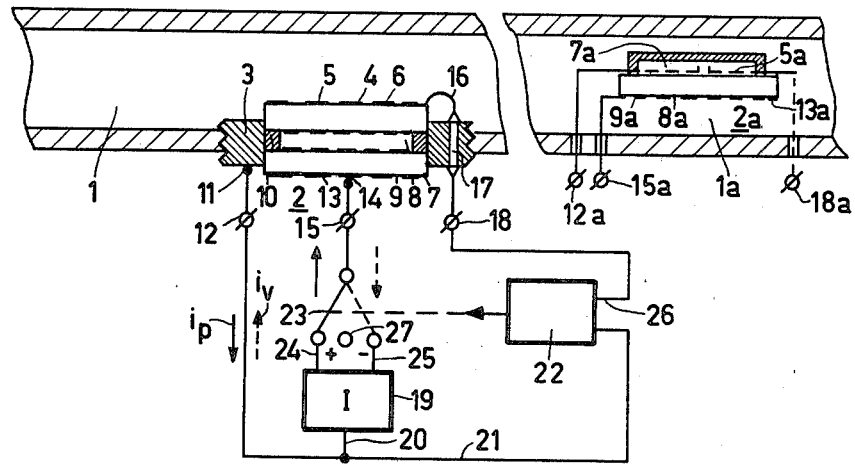
Figure 2:
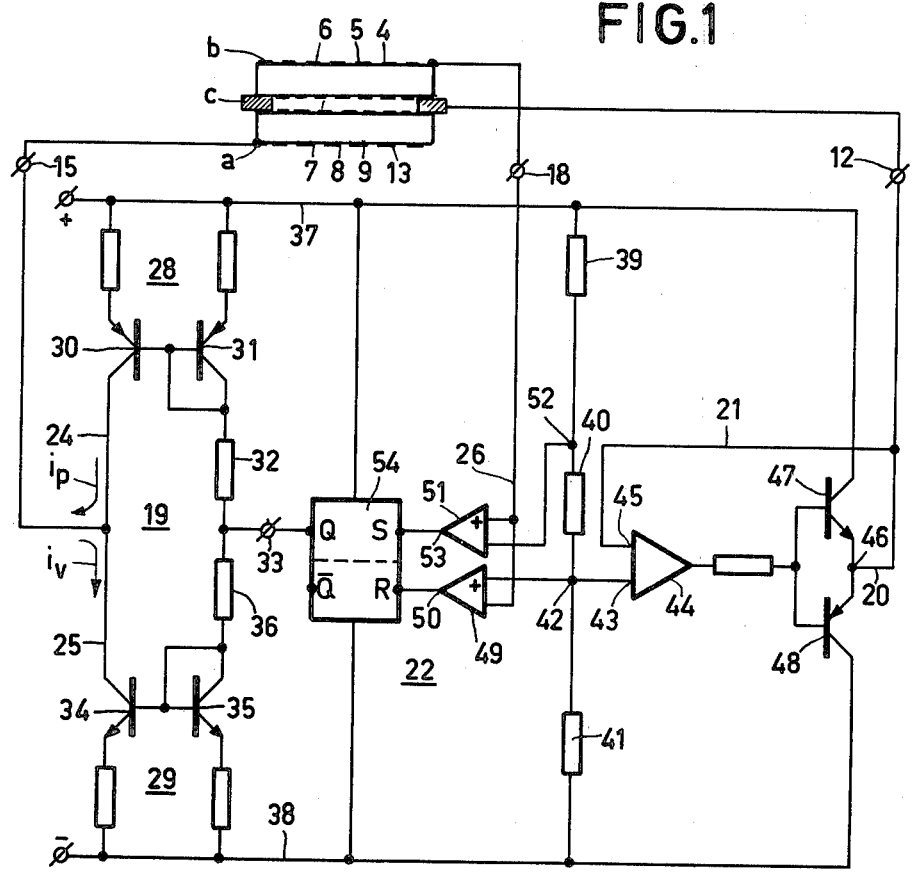
Figure 3:
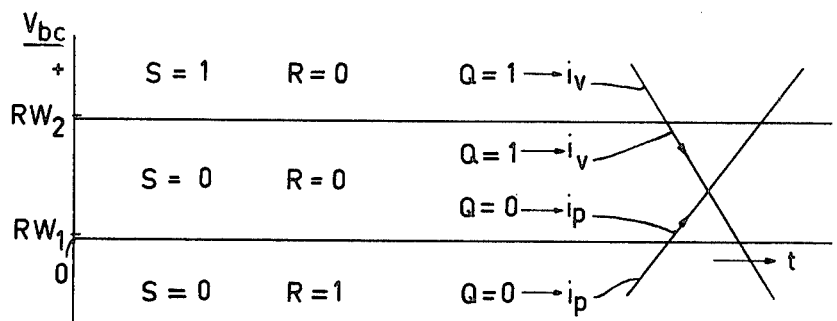
Figure 4:
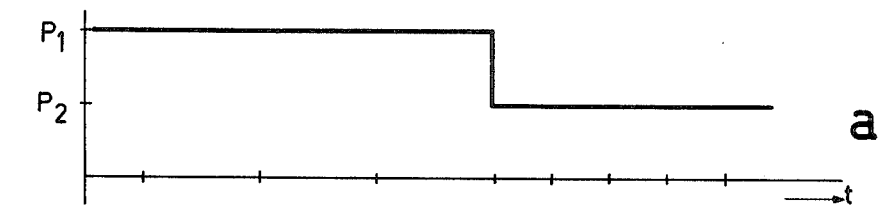
FIG. 4 illustrates four time diagrams, a, b, c and d which represent the variation of the pressure in the first space, the pumping and filling currents $i_p$ and $i_v$ respectively, which currents have been selected to be equal, the voltage Vbc across the partition 4, and the voltage Vac across the partition 8.
Figure 4:
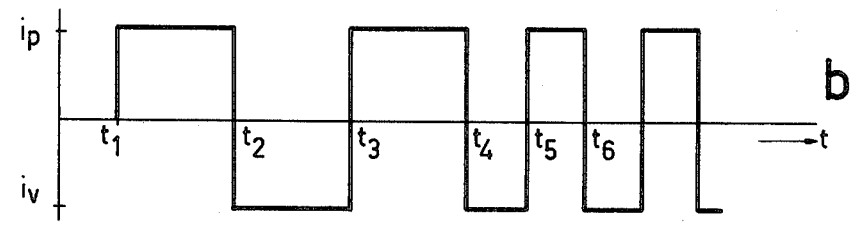
Figure 4:
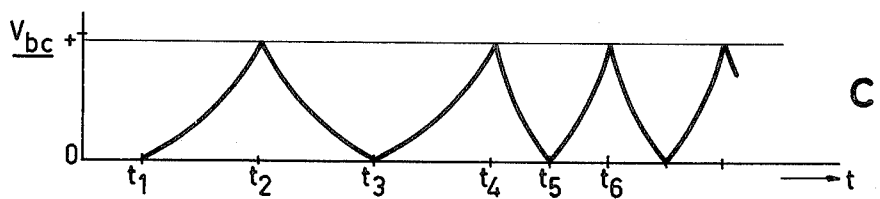
Figure 4:
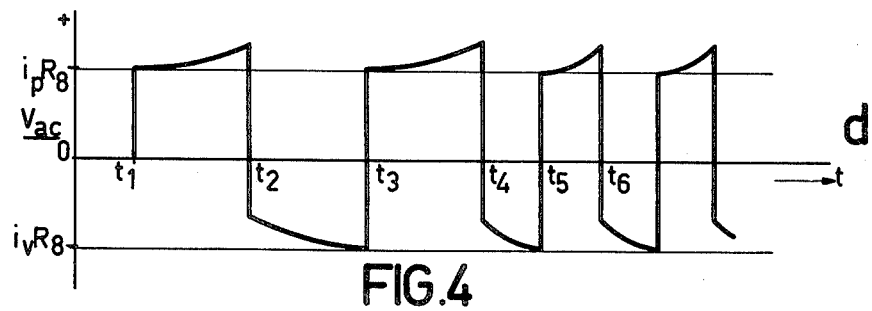

In FIG. 4b the currents obtained from the current sources are plotted. The current value may for example be 10 mA. The area of the current blocks represents charge and is proportional to the charge transferred in the partition. In FIG. 4c the voltage across the measuring partition is plotted. This voltage oscillates between the two reference values and thus determines the time intervals for filling and emptying the measuring space. The measurement of the time intervals $t_2-t_1$, $t_3-t_2$ or $t_3-t_1$ and $t_5-t_4$, $t_6-t_5$ or $t_6-t_4$ yields the information representing the concentration of the gaseous component.

The voltage across the other partitions is represented in FIG. 4d. A substantial part of the voltage results from the voltage drop which is produced across the internal resistance R 8 of partition 8 by the current. The other part is the Nernst voltage and thus exhibits the same pattern as the voltage Vbc in FIG. 4c. If the voltage $V_{ac}$ were employed for detection purposes, it would therefore be desirable to subtract the relevant voltage drops from $V_{ac}$ before comparing said voltage with the reference values.

It appears that the dimensions of the measurement space can be made very small, thickness 10 micrometers, diameter 5 millimeters. At an operating temperature of 700° C., currents of 10 mA and reference values of zero and of some tens of millivolts, a cycle time $t_3-t_1$ can be obtained for zirconium oxide as the partition material, which time interval is of the order of milliseconds to some tens of milliseconds for exhaust gases of internal combustion engines.

This very fast response time and the small dimensions are found to be very advantageous.

What is claimed is:

1. A gas analysis apparatus for measuring the concentration of a gaseous component in a first space comprising, means defining a measurement space hermetically sealed with respect to the first space and having at least one wall portion that comprises a partition which at least partly separates the measurement space from the first space and which comprises at least one solid substance exhibiting ionic conduction, at least one electrode layer on each side of the partition, means connecting said electrode layers to a control unit which periodically applies a pumping current to the partition during a pumping time interval $t_p$ so that a current of ions flows in the partition whereby the gaseous component is removed from the measurement space, the control unit subsequently applying a filling current of a polarity opposite to that of the pumping current to the partition in a filling time interval $t_v$ during which the measurement space is refilled to the concentration to be measured, the electric charge transferred in the partition being a measure of the concentration of the gaseous component, and a detection circuit connected to electrode layers of the partition for producing an interrupt signal for interrupting the current supplied by the control unit for a specific voltage variation between said electrode layers, the detection circuit comprising a first voltage detector connected to electrode layers of the partition for supplying a filling-interrupt signal for interrupting the filling current when the voltage across said electrode layers has reached a first reference value at which the concentration of the gaseous component on both sides of the partition is substantially the same.

2. A gas analysis apparatus as claimed in claim 1, wherein the detection circuit further comprises a second voltage detector which supplies a pumping-interrupt signal for interrupting the pumping current when the voltage across the said electrode layers of the partition exceeds a second reference value.

3. A gas analysis apparatus as claimed in claim 2 wherein the control unit further comprises a flip-flop having a set input and a reset input, means connecting said inputs to the first and the second voltage detectors for receiving the filling-interrupt signal and the pumping-interrupt signal, respectively, and means connecting at least one output of the flip-flop to a current supply unit which alternately supplies the filling current and the pumping current to the partition depending on the state of the flip-flop.

4. A gas analysis apparatus as claimed in claim 3 wherein the current supply unit comprises first and second current source circuits which supply the pumping current and the filling current, respectively, the period of a pulse train obtained at one output of the flip-flop being a measure of the concentration of the gaseous component to be measured.

5. A gas analysis apparatus as claimed in claims 1, 2, 3 or 4 further comprising a second partition having electrode layers on opposite sides thereof connected to the control unit whereby the second partition alternately receives the filling current and the pumping current.

6. A gas analysis apparatus as claimed in claim 1 wherein said detection circuit includes means for deriving a periodic signal determined by said interrupt signals such that the period of said periodic signal is dependent on the concentration of said gaseous component within said first space.

7. A gas analysis apparatus for determining the concentration of a gas component within a first space comprising, a chamber that defines a measurement space having a wall portion that includes a partition separating the measurement space from the first space and which comprises a solid substance exhibiting ionic conduction, first and second electrode means contacting opposite surfaces of said partition, a control unit coupled to said first and second electrode means to alternately apply a periodic current of opposite polarity to the partition during a pumping and a filling time interval so as to control the flow of the gas component to and from the measurement space by means of ion current flow in the partition, and the control unit includes a detection circuit coupled to at least one of said electrode means for deriving an interrupt signal that interrupts the current supplied by the control unit to the partition as a function of a signal produced at said one electrode means, said detection circuit deriving a filling-interrupt signal by means of which the control unit interrupts the supply of filling current to the partition when the signal at said one electrode means matches a first reference value indicating that the concentration of the gas components on both sides of the partition are substantially the same.

8. A gas analysis apparatus as claimed in claim 7 wherein the detection circuit further comprises a first voltage detector having said first reference value indicating equality of the concentration of the gas components on both sides of the partition and a second voltage detector having a second reference value indicative of a measurement space depleted of said gas component to a given level, and means connecting an input of the first and second detectors to the one electrode means of the partition for deriving a filling-interrupt signal and a pumping-interrupt signal by means of which the control unit interrupts the supply of filling current and pumping current, respectively, to the partition when the signal at said one electrode means matches the first and second reference values, respectively.

9. A gas analysis apparatus as claimed in claim 8 wherein the control unit includes a terminal at which a periodic signal appears having a period that is determined by the time of occurrence of said interrupt signals, the relative time of occurrence of the interrupt signals being dependent on the concentration of said gas component whereby the period of the periodic signal at said terminal is indicative of the concentration of said gas component within said first space.

10. A gas analysis apparatus as claimed in claim 8 wherein said second reference value is chosen so that at the end of a pumping time interval the measurement space is completely emptied of said gas component.

11. A gas analysis apparatus as claimed in claims 7 or 8 wherein said control unit includes a current supply unit coupled to said first and second electrode means and switching means coupled to an output of the detection circuit for alternately reversing the polarity of the current supplied by the current supply unit to said partition in response to interrupt signals.

12. A gas analysis apparatus as claimed in claim 7, wherein said chamber is hermetically sealed so as to prevent the continuous diffusion of said gas component into said measurement space.

13. A gas analysis apparatus as claimed in claim 7 wherein said chamber is hermetically sealed to prevent the passage of said gas component between the measurement space and the first space and said control unit includes means responsive to a flow of ionic current in the partition for deriving a signal indicative of the concentration of the gas component within said first space.

14. A gas analysis apparatus for determining the concentration of a gas component within a first space comprising, a chamber that defines a measurement space having a wall portion that includes first and second partitions each comprising a solid substance exhibiting ionic conduction, the first partition separating the measurement space from the first space and the second partition separating the measurement space from a reference space, electrode means contacting opposite surfaces of said first and second partitions, a control unit coupled to said electrode means to alternately apply a pumping current and a filling current of opposite polarity to the second partition during a pumping and a filling time interval, respectively, for alternately removing and filling the gas component in the measurement space by means of ion current flow in the second partition, and the control unit includes a detection circuit coupled to said electrode means for deriving alternate filling-interrupt and pumping-interrupt signals that cause the control unit to interrupt and reverse the polarity of current supplied to the second partition thereby deriving said opposite polarity pumping and filling currents.

15. A gas analysis apparatus as claimed in claim 14 wherein the electrode means includes first and second electrodes on the outside and inside surfaces respectively of the first partition, third and fourth electrodes on the inside and outside surfaces respectively of the second partition, said apparatus further comprising a conductor ring within the measurement space for electrically interconnecting the second and third electrodes, and wherein an input of the detection circuit is coupled to the first and second electrodes and the control unit is coupled to the third and fourth electrodes to supply thereto said opposite polarity pumping and filling currents.

16. A gas analysis apparatus as claimed in claims 14 or 12 wherein the control unit includes a current supply unit controlled by said interrupt signals for supplying approximately equal amplitude pumping and filling currents to the second partition so that the filling time period and the pumping time period are substantially equal.

17. A gas analysis apparatus for determining the concentration of a gas component within a first space comprising, a chamber that defines a measurement space having a wall portion that includes first and second partitions each comprising a solid substance exhibiting ionic conduction, the first partition separating the measurement space from the first space and the second partition separating the measurement space from a reference space, electrode means contacting opposite surfaces of said first and second partitions, a control unit coupled to said electrode means to alternately apply a filling current and a pumping current of opposite polarity to one of said partitions during a filling and a pumping time interval, respectively, for alternately filling and removing the gas component in the measurement space by means of ion current flow in said one partition, and the control unit includes a detection circuit coupled to said electrode means for deriving alternate filling-interrupt and pumping-interrupt signals that cause the control unit to interrupt and reverse the polarity of current supplied to said one partition thereby deriving said opposite polarity filling and pumping currents, said detection circuit deriving said filling-interrupt signal when the concentration of the gas components within the measurement space and the first space are substantially equal.

18. A gas analysis apparatus as claimed in claim 17 wherein said one partition comprises the second partition.

19. A gas analysis apparatus as claimed in claim 18, wherein said control unit includes means coupled to the electrode means of the first partition for measuring the Nernst voltage developed thereacross.

20. A gas analysis apparatus as claimed in claims 17 or 15, wherein the control unit includes a terminal at which a periodic signal appears that is determined by the time of occurrence of said interrupt signals, the relative time of occurrence of the interrupt signals being dependent on the concentration of said gas component whereby the period of said periodic signal is indicative of the concentration of said gas component within said first space.

21. A gas analysis apparatus as claimed in claims 17 or 15, wherein the control unit includes a current supply unit controlled by said interrupt signals for supplying pumping and filling currents of constant magnitude to said one partition such that the filling time period is of the same order of magnitude or is smaller than the pumping time period.

22. A gas analysis apparatus as claimed in claims 14 or 17 wherein said control unit provides pumping and filling currents which together produce a periodic current waveform.

* * * * *